US00PP21311P2

(12) United States Plant Patent
Yates

(10) Patent No.: US PP21,311 P2
(45) Date of Patent: Sep. 21, 2010

(54) ***ARGYRANTHEMUM* PLANT NAMED 'ARG B07'**

(50) Latin Name: *Argyranthemum hybrida*
Varietal Denomination: ARG B07

(76) Inventor: Fred Yates, Holmes Chapel Road, Somerford, Congleton, Cheshire, CW12 4SP (GB)

( * ) Notice: Subject to any disclaimer, the term of this patent is extended or adjusted under 35 U.S.C. 154(b) by 0 days.

(21) Appl. No.: 12/454,019

(22) Filed: May 11, 2009

(51) Int. Cl.
*A01H 5/00* (2006.01)

(52) U.S. Cl. ..... Plt./406
(58) Field of Classification Search ..... Plt./406, Plt./284
See application file for complete search history.

*Primary Examiner*—June Hwu
(74) *Attorney, Agent, or Firm*—C. A. Whealy

(57) ABSTRACT

A new and distinct cultivar of *Argyranthemum* plant named 'ARG B07', characterized by its compact, upright to outwardly spreading and mounded plant habit; freely branching growth habit; dense and bushy habit; freely flowering habit; semi-double-type inflorescences with bright yellow-colored ray florets and darker yellow-colored disc florets; and good garden performance.

3 Drawing Sheets

Botanical designation: *Argyranthemum hybrida.*
Cultivar denomination: 'ARG B07'.

BACKGROUND OF THE INVENTION

The present invention relates to a new and distinct cultivar of *Argyranthemum* plant, botanically known as *Argyranthemum hybrida* and hereinafter referred to by the name 'ARG B07'.

The new *Argyranthemum* plant is a naturally-occurring whole plant mutation of an unidentified selection of *Argyranthemum hybrida*, not patented. The new *Argyranthemum* was discovered and selected by the Inventor as a single flowering plant from within a population of plants of the parent selection in a controlled greenhouse environment in Swavesey, Cambridgeshire, United Kingdom in June, 2005.

Asexual reproduction of the new *Argyranthemum* plant by vegetative cuttings in a controlled greenhouse environment in Swavesey, Cambridgeshire, United Kingdom since the spring of 2006 has shown that the unique features of this new *Argyranthemum* plant are stable and reproduced true to type in successive generations.

SUMMARY OF THE INVENTION

Plants of the new *Argyranthemum* have not been observed under all possible environmental conditions. The phenotype may vary somewhat with variations in environment such as temperature and light intensity, without, however, any variance in genotype.

The following traits have been repeatedly observed and are determined to be the unique characteristics of 'ARG B07'. These characteristics in combination distinguish 'ARG B07' as a new and distinct cultivar of *Argyranthemum:*

1. Compact, upright to outwardly spreading and mounded plant habit.
2. Freely branching growth habit; dense and bushy habit.
3. Freely flowering habit.
4. Semi-double-type inflorescences with bright yellow-colored ray florets and darker yellow-colored disc florets.
5. Good garden performance.

Plants of the new *Argyranthemum* differ from plants of the parent selection primarily in the following characteristics:

1. Plants of the new *Argyranthemum* are more compact than plants of the parent selection.
2. Plants of the new *Argyranthemum* are more freely branching than plants of the parent selection.
3. Plants of the new *Argyranthemum* are more freely flowering than plants of the parent selection.

Plants of the new *Argyranthemum* can be compared to plants of the *Argyranthemum* 'Butterfly', not patented. In side-by-side comparisons conducted in Swavesey, Cambridgeshire, United Kingdom, plants of the new *Argyranthemum* differed from plants of 'Butterfly' in the following characteristics:

1. Plants of the new *Argyranthemum* were more compact than and plants of 'Butterfly'.
2. Plants of the new *Argyranthemum* were more freely branching than plants of 'Butterfly'.
3. Plants of the new *Argyranthemum* were more freely flowering than plants of 'Butterfly'.
4. Plants of the new *Argyranthemum* were more heat tolerant than plants of 'Butterfly'.

BRIEF DESCRIPTION OF THE PHOTOGRAPHS

The accompanying photographs illustrate the overall appearance of the new *Argyranthemum*. These photographs show the colors as true as it is reasonably possible to obtain in colored reproductions of this type.

Colors in the photographs may differ slightly from the color values cited in the detailed botanical description which accurately describe the colors of the new *Argyranthemum* plant.

The photograph on the first sheet comprises a side perspective view of a typical flowering stem of 'ARG 07'.

The photographs on the second and third sheets are close-up views of typical inflorescences of 'ARG B07'.

DETAILED BOTANICAL DESCRIPTION

The aforementioned photographs and following observations and measurements describe plants grown in a glass-covered greenhouse during the spring and summer in Swavesey, Cambridgeshire, United Kingdom and under conditions and practices which approximate those generally used in commercial *Argyranthemum* production. During the production of the plants, day temperatures averaged 25° C. and night temperatures averaged 16° C. Rooted young plants were planted in 16-cm containers and had been growing for one month when the photographs were taken and had been growing for five months when the description was taken. In the following description, color references are made to The Royal Horticultural Society Colour Chart, 2001 Edition, except where general terms of ordinary dictionary significance are used.

Botanical classification: *Argyranthemum hybrida* 'ARG B07'.

Parentage: Naturally-occurring whole plant mutation of an unidentified selection of *Argyranthemum hybrida*, not patented.

Propagation:

*Type.*—Vegetative tip cuttings.

*Time to initiate roots, summer.*—About five to seven days at temperatures of 22° C.

*Time to initiate roots, winter.*—About seven to ten days at temperatures of 20° C.

*Time to produce a rooted young plant, summer.*—About 12 to 16 days at temperatures of 22° C.

*Time to produce a rooted young plant, winter.*—About 18 to 22 days at temperatures of 20° C.

*Root description.*—Fleshy, medium in thickness; white in color.

*Rooting habit.*—Freely branching; moderately dense.

Plant description:

*Appearance.*—Herbaceous semi-double-type potted *Argyranthemum*; compact, upright to outwardly spreading and mounded plant habit; freely branching growth habit; dense and bushy habit.

*Plant height.*—About 40 cm.

*Lateral branches.*—Length: About 35 cm. Diameter: About 4 mm. Internode length: About 1 cm to 1.5 cm. Texture: Smooth, glabrous; longitudinally ridged. Angle: About 45° from vertical. Color: Close to 144A.

Foliage description:

*Arrangement.*—Alternate, simple; sessile.

*Length.*—About 6.5 cm.

*Width.*—About 3.5 cm.

*Shape.*—Deeply pinnate or bipinnate.

*Apex.*—Apiculate.

*Base.*—Narrowly acuminate.

*Margin.*—Senate; deeply incised.

*Texture, upper and lower surfaces.*—Smooth, glabrous; leathery.

*Venation pattern.*—Pinnate.

*Color.*—Developing and fully expanded leaves, upper surface: Close to 137A; towards the base, close to 143C; venation, close to 137A. Developing and fully expanded leaves, lower surface: Close to 137B; venation, close to 138B.

Inflorescence description:

*Appearance.*—Semi-double-type inflorescence form with lanceolate to obovate-shaped ray florets; inflorescences borne on terminal and axillary peduncles above foliage; disc and ray florets arranged acropetally on a capitulum; freely flowering habit.

*Fragrance.*—None detected.

*Flowering season.*—Plants begin flowering during the summer and continue flowering until the end of October in Cambridgeshire, United Kingdom; inflorescences persistent.

*Inflorescence bud.*—Height: About 9 mm. Diameter: About 9 mm. Shape: Ovoid. Color: Close to 6B.

*Inflorescence size.*—Diameter: About 6.5 cm. Depth (height): About 2 cm. Diameter of disc: About 1.5 cm.

*Ray florets.*—Orientation: About 30° from the peduncle axis, eventually perpendicular to the peduncle; flat with apices reflexing with development. Length: About 3 cm. Width: About 9 mm. Shape: Lanceolate to obovate. Apex: Rounded. Base: Acute. Margin: Entire. Texture, upper and lower surfaces: Smooth, glabrous; longitudinally ridged. Number of ray florets per inflorescence: About 21 arranged in two whorls. Color: When opening and fully opened, upper surface: Close to 5A. When opening and fully opened, lower surface: Close to 8B.

*Disc florets.*—Arrangement: Numerous disc florets massed at center of receptacle. Shape: Tubular, elongated. Apex: Five-pointed. Length: About 5 mm. Width: About 1 mm. Color, immature and mature: Close to 17A.

*Phyllaries.*—Number of phyllaries per inflorescence: About 30. Length: About 6 mm Width: About 4 mm. Shape: Ovate to deltoid. Apex: Obtuse. Margin: Entire, papery. Texture, upper and lower surfaces: Smooth, glabrous. Color, upper surface: Close to 137C.

*Peduncles.*—Length, terminal peduncle: About 6.5 cm. Diameter, terminal peduncle: About 2 mm. Texture: Smooth, glabrous; longitudinally ridged. Color: Close to 137D.

*Reproductive organs.*—Androecium (present on disc florets only): Quantity per disc floret: Five. Filament length: About 1.5 mm. Filament color: Close to 4C. Anther shape: Lanceolate. Anther length: About 1.5 mm. Anther diameter: Less than 0.5 mm. Anther color: Close to 13B. Pollen amount: None observed. Gynoecium (present on ray and disc florets): Stigma shape: Two-parted. Stigma color: Close to 17B. Style length: About 3 mm. Style color: Close to 13A. Ovary color: Close to 145D.

*Seed/fruit.*—Seed and fruit production has not been observed.

Disease/pest resistance: Resistance to pathogens and pests common to *Argyranthemums* has not been observed on plants grown under commercial conditions.

Garden performance: Plants of the new *Argyranthemum* have been observed to have good garden performance and to tolerate strong winds, rain and temperatures ranging from about −2° C. to 3° C. to about 35° C. to 38° C.

It is claimed:

1. A new and distinct *Argyranthemum* plant named 'ARG B07' as illustrated and described.

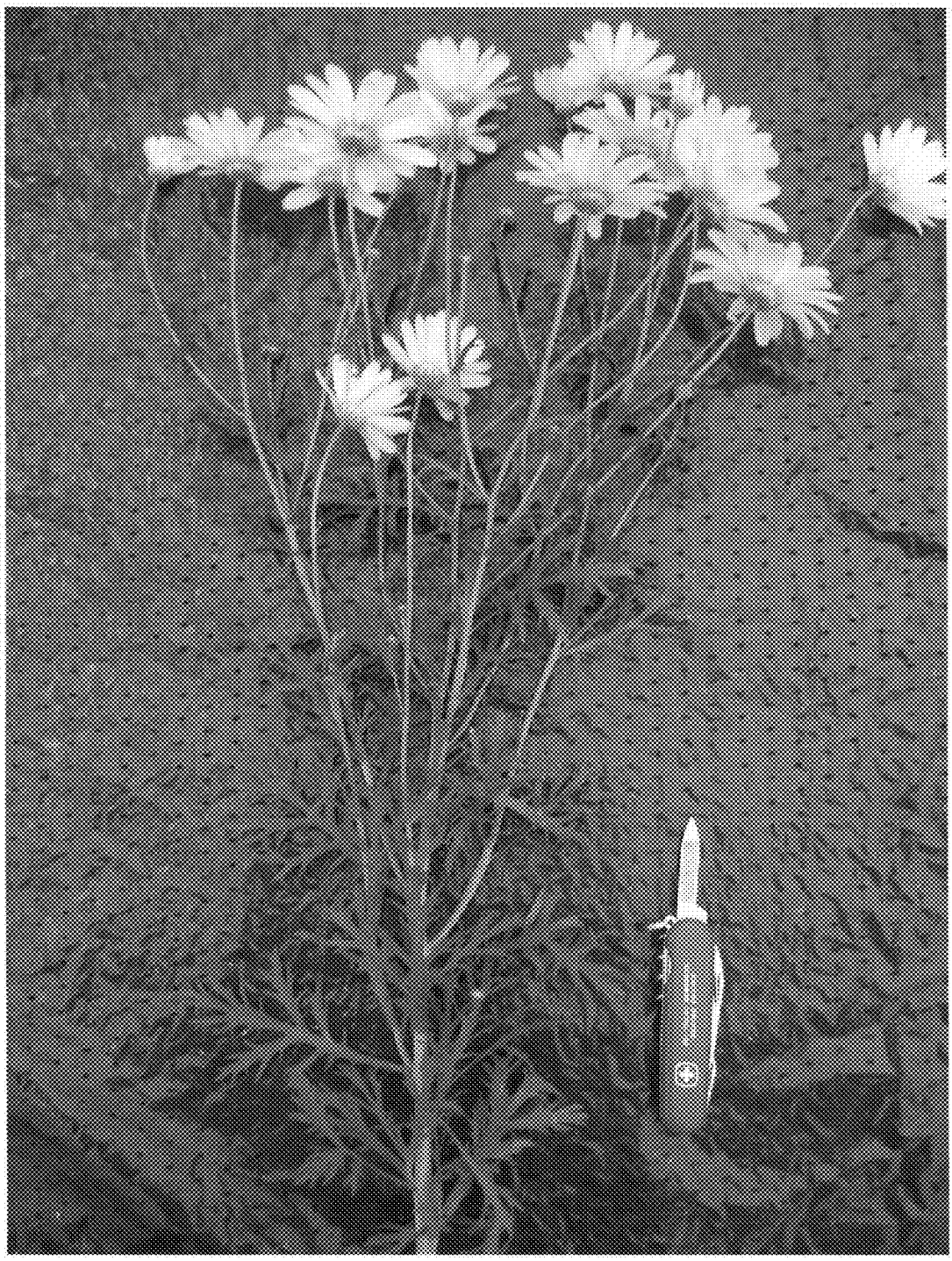

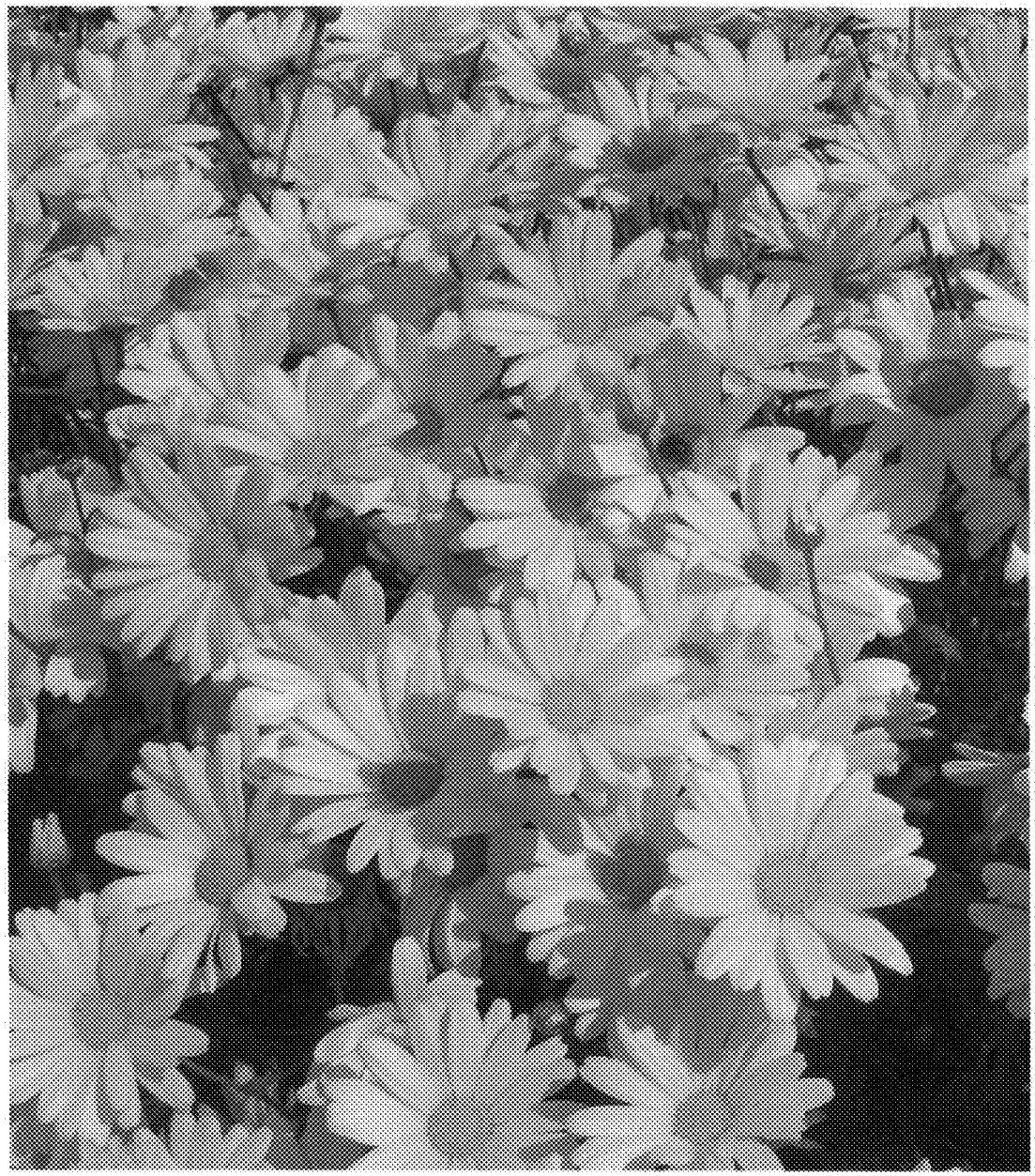

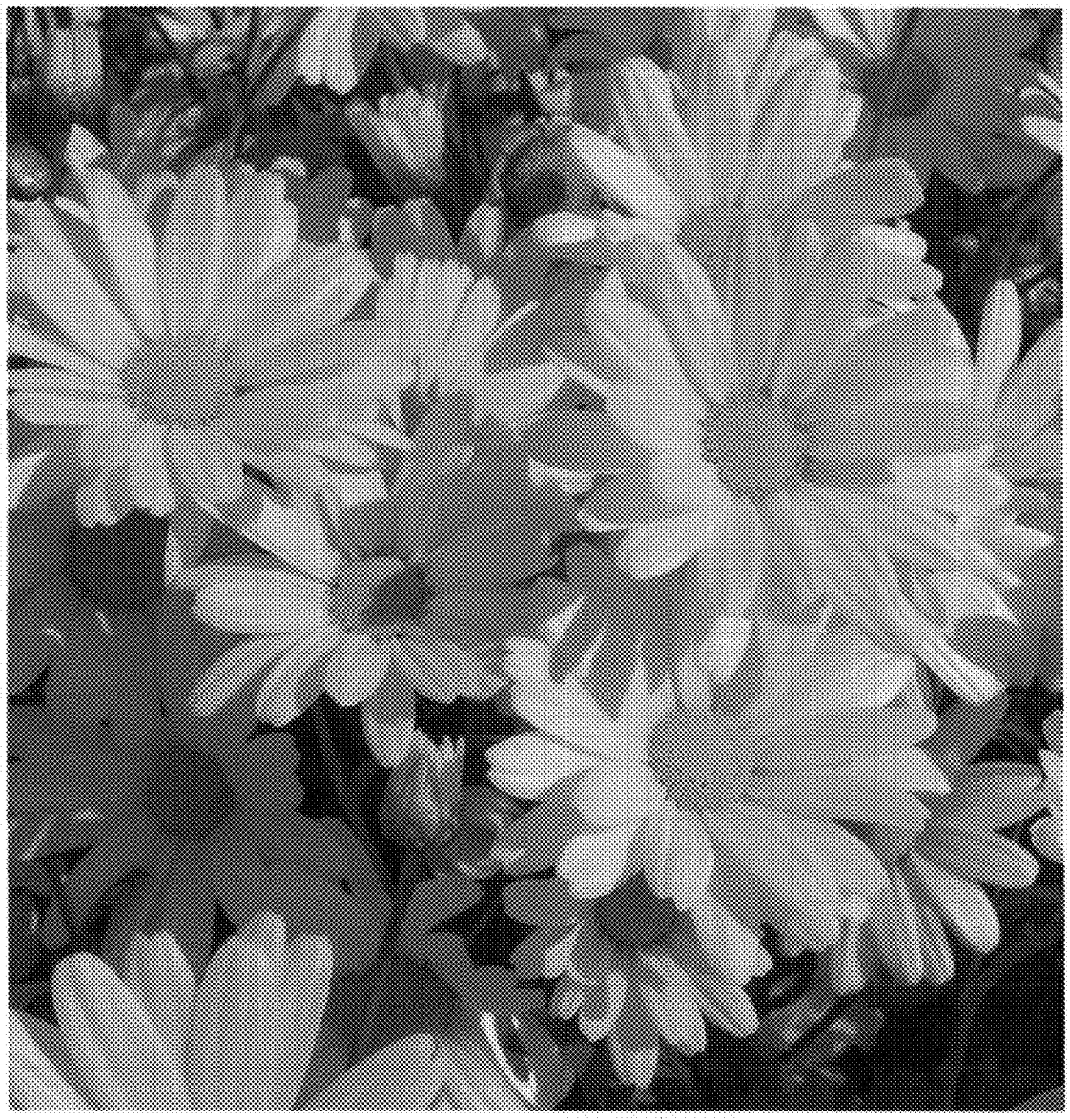

* * * * *